US00PP35661P2

(12) United States Plant Patent
Van Swieten

(10) Patent No.: US PP35,661 P2
(45) Date of Patent: Feb. 20, 2024

(54) ***PHALAENOPSIS* ORCHID PLANT NAMED 'PHA601241'**

(50) Latin Name: ***Phalaenopsis* hybrid**
Varietal Denomination: PHA601241

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,297

(22) Filed: Jun. 22, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHA601241', particularly characterized by having numerous attractive, large, light purple, striped flowers with reddish-purple lips, flowers that are flat in lateral view, and weak lip curvature of the lateral lobes, is disclosed.

3 Drawing Sheets

Genus and species: *Phalaenopsis* hybrid.
Variety denomination: 'PHA601241'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA601241'.

The new *Phalaenopsis* plant is a product of a planned breeding program conducted by the inventor in Bleiswijk, the Netherlands. The objective of this breeding program was to create a new *Phalaenopsis* plant with numerous attractive, large, light purple, striped flowers with reddish-purple lips suitable for potted plant production.

The new *Phalaenopsis* plant 'PHA601241' is a result of cross-pollination made by the inventor in April 2015 in Bleiswijk, the Netherlands, of the proprietary female, or seed parent, *Phalaenopsis* hybrid '00001-5221' (unpatented), with a proprietary male, or pollen parent, *Phalaenopsis* hybrid '12-050809-0001' (unpatented).

The new *Phalaenopsis* was selected by the inventor as a single plant within the progeny of the stated cross-pollination in a controlled greenhouse in Bleiswijk, the Netherlands, in December 2017. Asexual reproduction of the new *Phalaenopsis* plant by meristem tissue culture since 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 20, 2022 (Application no. 2022/0177), by Applicant who obtained the subject matter disclosed directly from the inventor. 'PHA601241' has not been made publicly available or sold anywhere in the world prior to the effective filing date of this application with the exception of sales or disclosures made one year or less before the effective filing date of this claimed invention by Applicant who obtained 'PHA601241' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA601241' as a new and distinct variety of *Phalaenopsis* plant:

1) large, light purple, striped flowers with reddish-purple lips;
2) flower shape in lateral view is flat; and
3) lip curvature of lateral lobes is weak.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2023. Colors in the photographs may differ from the color values cited in the detailed botanical description, which accurately describe the actual colors of the new variety.

DESCRIPTION OF THE NEW VARIETY

Figure 1:
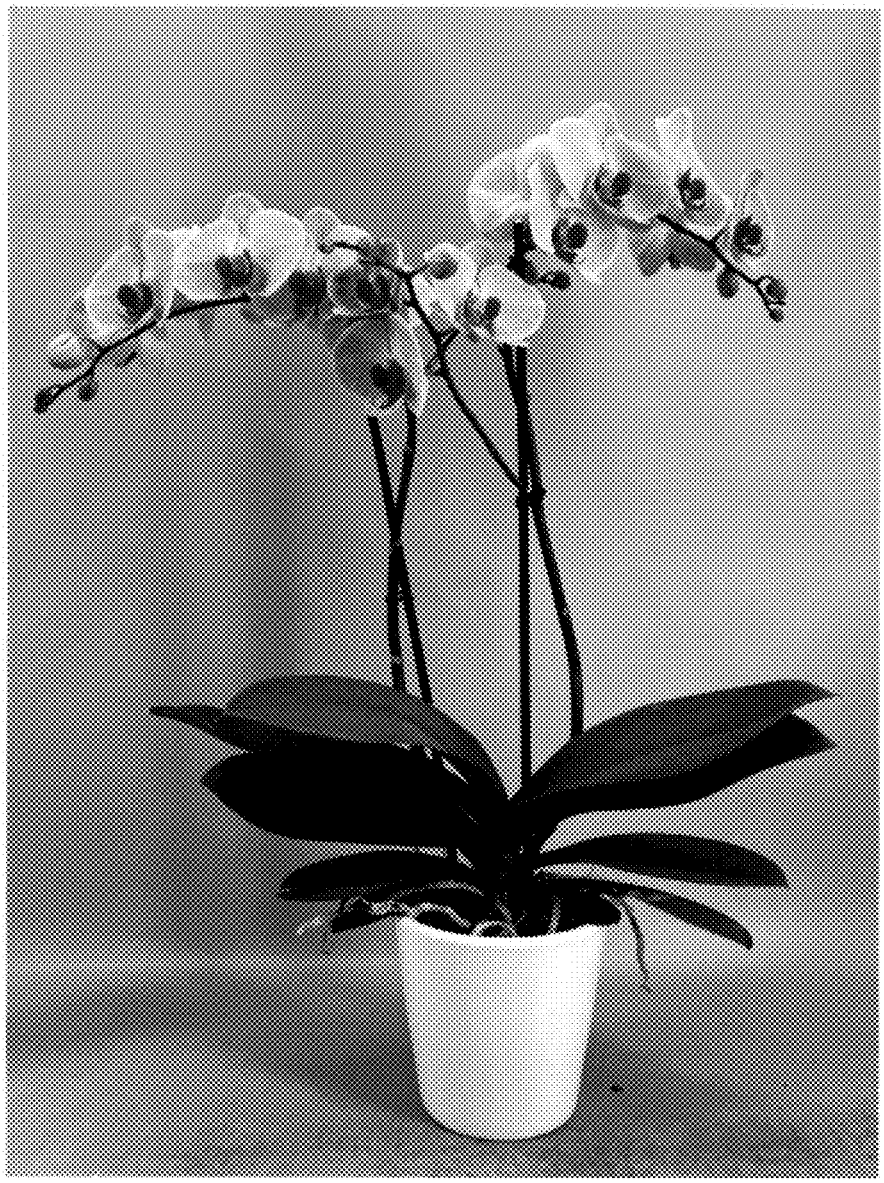
FIG. 1 shows the overall plant habit, including blooms, buds, and foliage of 'PHA601241'.
Figure 2:
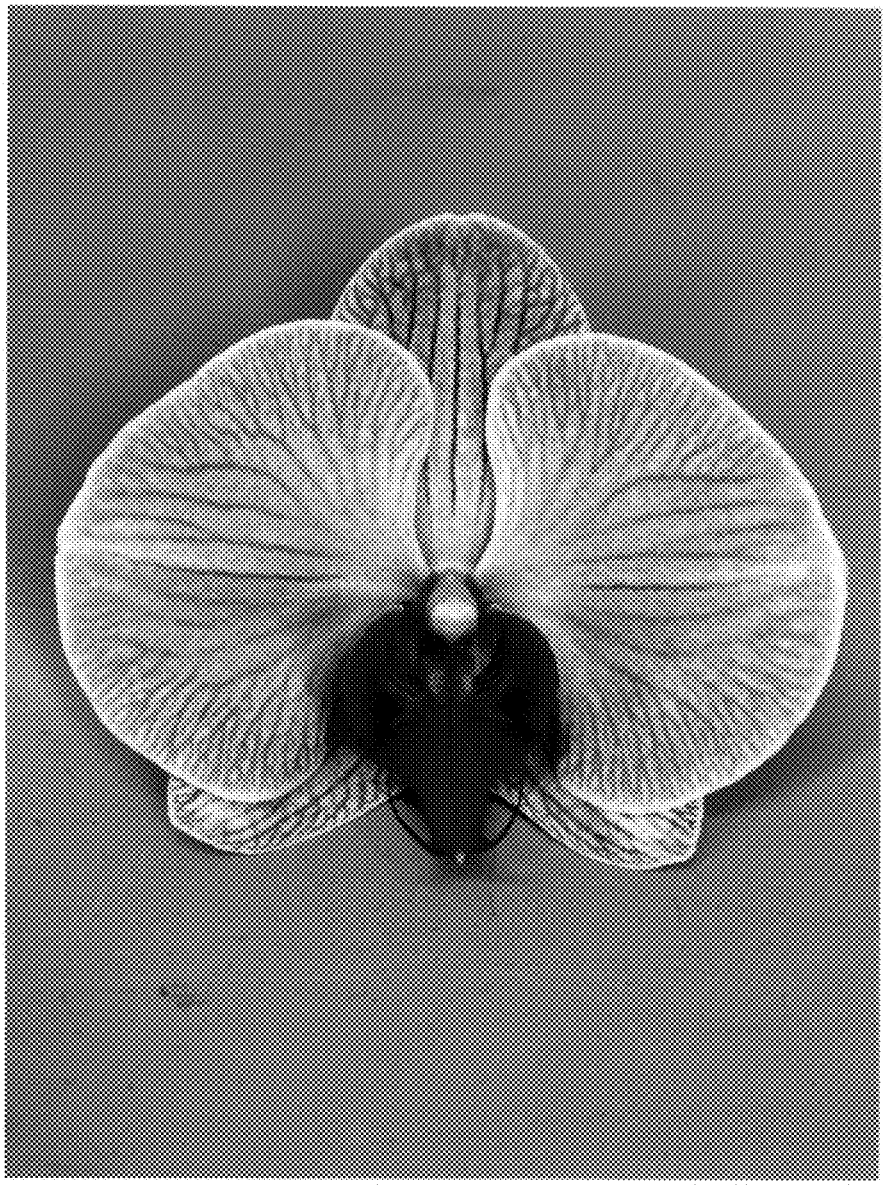
FIG. 2 shows a close-up of a flower of 'PHA601241'.
Figure 3:
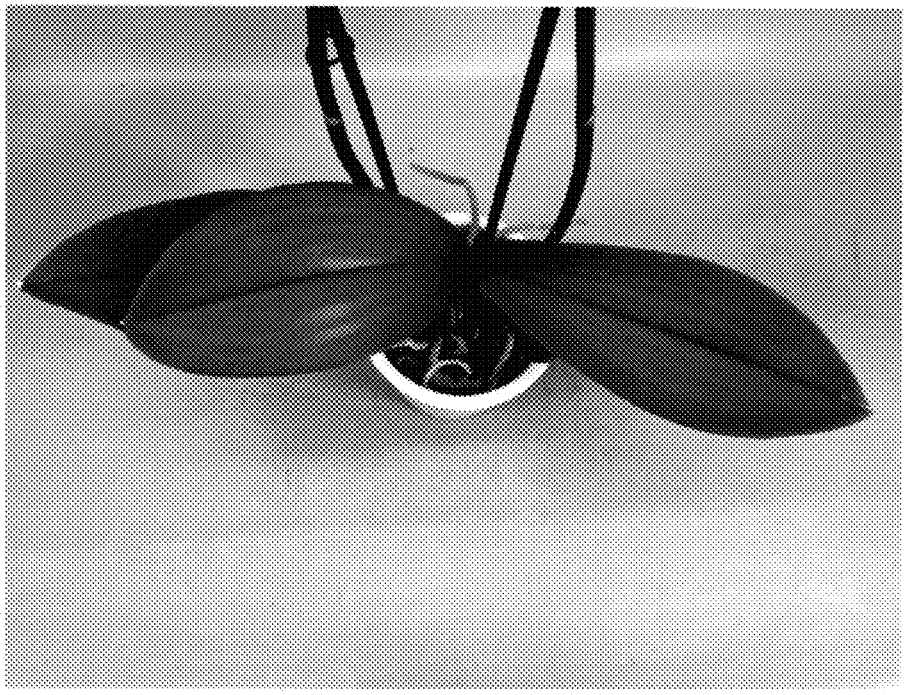
FIG. 3 shows a close-up, overhead view of the leaves of 'PHA601241'.

The following detailed description sets forth the distinctive characteristics of 'PHA601241'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 1.2 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA601241'.

Parentage:

*Female parent*.—*Phalaenopsis* cultivar '00001-5221' (unpatented).

*Male parent*.—*Phalaenopsis* cultivar '12-050809-0001' (unpatented).

Propagation:

*Type*.—Meristem tissue culture.

Roots:

*Root description*.—Greyed-green colored roots (a color in between RHS 190B and RHS 190C) with branching lateral roots having light yellow-green (RHS 145C) with a touch of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 62.0 cm to 67.0 cm.

*Width* (*measured from leaf tips*).—About 41.0 cm to 43.0 cm.

*Vigor*.—Strong.

Leaves:

*Mature leaves*.—Quantity per plant: 9 to 10 leaves are produced before flowering. Length (fully expanded): 22.0 cm to 24.0 cm. Width: 8.5 cm to 9.5 cm. Position of the broadest part of the leaf: At the middle. Shape: Oblong. Base shape: Moderately elongated. Apex: Obtuse asymmetric. Leaf blade angle with the petiole (measured from the horizontal position): Between 30 degrees and 45 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 144A.

Peduncle:

*Quantity per plant*.—2.

*Number of flowers per peduncle*.—23 to 28.

*Length*.—62.0 cm to 67.0 cm.

*Diameter*.—7.0 mm to 8.0 mm.

*Strength*.—Strong.

*Aspect*.—Upright to slightly pendent.

*Texture*.—Smooth.

*Color*.—Mix of reddish-brown (RHS 200B) and yellow-green (RHS 146D).

*Internode length*.—2.5 cm to 3.0 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip): 380.0 mm to 430.0 mm.

*Flowering time*.—First flowers can be expected 10 to 11 months after planting in a 12-cm pot.

*Flower*.—Height: 85.0 mm to 90.0 mm. Diameter: 100.0 mm to 105.0 mm. Depth of lip: 24.0 mm to 26.0 mm.

*Flower shape*.—Flat.

*Flower longevity*.—On the plant: 9 to 11 weeks.

*Fragrance*.—Absent.

*Flower bud*.—Average size: Large. Length: 25.0 mm to 27.0 mm. Width: 23.0 mm to 25.0 mm. Shape: Egg shaped. Color: Light yellow-green (a color in between RHS 145C and RHS 160C) with diluting purplish-red stripes and shade (RHS 186B).

*Petals*.—Arrangement: Open/free. Shape: Moderately compressed. Apex: Rounded asymmetric. Margin: Entire. Length (from base to tip): 45.0 mm to 47.0 mm. Width: 62.0 mm to 64.0 mm. Position of the broadest part of the petal: Toward the base. Color (when fully opened): Upper surface: Basic color: Light purple (RHS 76A). Over color: Few reddish-purple stripes (RHS N78B) at the middle; purplish-pink stripes and netting (RHS N78C); white small margin (RHS NN155C). Lower surface: Basic color: Very light purple (RHS 76B). Over color: Light reddish-purple stripes (RHS N78D); white region (RHS NN155D) at the middle. Number of spots and stripes on the lateral sepals (upper surface): Many. Color of spots and stripes on the lateral sepals (upper surface): Few reddish-purple stripes (RHS N78B); purplish-pink (RHS N78C) toward margins. Density of netting of the lateral sepals (upper surface): None. Color of the netting (upper surface): Purplish-pink (RHS N78C).

*Dorsal sepal*.—Shape: Broad elliptic. Apex: Emarginated symmetric. Margin: Entire. Length (from base to tip): 57.0 mm to 59.0 mm. Width: 37.0 mm to 39.0 mm. Position of the broadest part of the dorsal sepals: At middle. Color (when fully opened): Upper surface: Basic color: Very light purple (RHS 76B). Over color: Reddish-purple stripes (RHS N78B) and purplish-pink netting (RHS N78C). Lower surface: Basic color: Very light purple (RHS 76C). Over color: Yellow-green (RHS 145D) and diluting light purple netting (RHS 76A). Number of spots and stripes on the dorsal sepals (upper surface): Medium. Color of spots and stripes on the dorsal sepals (upper surface): RHS N78B. Density of netting of the dorsal sepals (upper surface): Medium. Color of the netting (upper surface): Purplish-pink (RHS N78C).

*Lateral sepals*.—Shape: Ovate. Apex: Obtuse asymmetric. Margin: Entire. Length (from base to tip): 49.0 mm to 51.0 mm. Width: 32.0 mm to 34.0 mm. Position of the broadest part of the lateral sepals: Toward the base. Color (when fully opened): Upper surface: Basic color: Very light purple (RHS 76B). Over color: Light yellow-green (RHS 145C); reddish-purple stripes (RHS N78B) and purplish-pink netting (RHS N78C). Lower surface: Basic color: Very light purple (RHS 76C). Over color: Light yellow-green (RHS 145D) and diluting very light purple netting (RHS 76B). Number of spots and stripes on the lateral sepals (upper surface): Medium. Color of spots and stripes on the lateral sepals (upper surface): Reddish-purple (RHS N78B). Density of netting of the lateral sepals (upper surface): Medium. Color of the netting (upper surface): Purplish-pink (RHS N78C).

*Labellum* (*lip*).—Whiskers: Present. Length of whiskers: 13.0 mm to 15.0 mm. Color of whiskers: Reddish-purple (RHS N78A) with purplish-red tips (RHS 61A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 22.0 mm to 24.0 mm. Width: 16.0 mm to 18.0 mm. Color: Upper surface: Touch of light greenish-yellow (RHS 4C) with dark red stripes (RHS 59A) at the base; dark reddish-orange (RHS 178B) from the base toward margin on one side; reddish-purple (RHS N78B) toward margin on the other side; light purple toward the tip (RHS 76A). Lower surface: White (RHS 155C) at the base toward margin on one side; dark reddish-orange (RHS 178B) toward margin on the other side; purplish-pink (RHS N78C) toward the tip. Number of spots and stripes on the lateral, lobe: Few stripes. Color of spots and stripes on the lateral lobe: Dark red (RHS 59A). Density of netting of the lateral lobe: None. Color of the netting: Not applicable.

*Apical lobe*.—Shape: Triangular. Margin: Entire. Length: 20.0 mm to 22.0 mm. Width: 26.0 mm to 28.0 mm. Color: Upper surface: Reddish-orange (a color in between RHS 178B and RHS 178C) at the base and toward wings; reddish-purple (RHS NN78A) toward whiskers. Lower surface: Reddish-orange margin (RHS 178C) at the base; white (RHS NN155D) at the middle from base toward whiskers; reddish-purple (RHS N78B) on sides toward whiskers. Number of spots and stripes on the apical lobe: None. Color of spots and stripes on the apical lobe: Not applicable. Density of netting of the apical lobe: None. Color of the netting: Not applicable. Bump and ridge (upper and lower surface): Absent.

*Callus*.—Average size: Medium to large. Height: 8.0 mm to 9.0 mm. Length: 7.0 mm to 8.0 mm. Width: 4.0 mm to 5.0 mm. Color: Light greenish-yellow (RHS 8C) on sides; reddish-orange (RHS 174B) on front side; yellow (RHS 17B) toward tips; dark reddish-orange spots and stripes (RHS 178B).

Reproductive organs:

*Column*.—Length: 10.0 mm to 11.0 mm. Diameter: 6.0 mm to 7.0 mm. Color: Light purple (RHS N75B).

*Pollinia*.—Quantity: 2. Diameter: 0.8 mm to 0.9 mm. Color: Orange (RHS 24A).

*Ovary*.—Length: 10.0 mm to 12.0 mm. Diameter: 2.6 mm to 3.0 mm.

*Pedicel*.—Length: 34.0 mm to 36.0 mm. Diameter: 3.1 mm to 3.6 mm. Color: Touch of brown (RHS 200C) at the base; yellow-green (RHS 146D) and light purple (RHS 75A) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA601241' differs from the female parent plant, cultivar '00001-5221' (unpatented), in that 'PHA601241' has wider flowers having no dots on the petals, and much longer plant length, whereas '00001-5221' has more narrow flowers with many dots on the petals, and shorter plant length.

'PHA601241' differs from the male parent plant, cultivar '12-050809-0001' (unpatented), in that 'PHA601241' has light purple petals with many stripes on the petals, and more narrow flowers, whereas '12-050809-0001' has white petals with no stripes on the petals, and wider flowers than 'PHA601241'.

'PHA601241' is most similar to the commercial *Phalaenopsis* plants named 'PHALGEXPA' (U.S. Plant Pat. No. 30,436) and 'PHALVAPYH' (U.S. Plant Pat. No. 31,052). 'PHA601241' differs from the commercial variety 'PHALGEXPA' in that 'PHA601241' has a wider flower, moderately compressed petals, and concave dorsal sepals, whereas 'PHALGEXPA' has a narrow flower, moderately compressed to medium petals, and straight dorsal sepals.

'PHA601241' differs from the commercial variety 'PHALVAPYH' in that 'PHA601241' has moderately compressed petals, medium length whiskers, and broad leaves, whereas 'PHALVAPYH' has moderately compressed to medium petals, short whiskers, and medium to broad leaves.

I claim:

1. A new and distinct variety of *Phalaenopsis* plant named 'PHA601241', substantially as described and illustrated herein.

* * * * *